United States Patent [19]
Van der Zel et al.

[11] Patent Number: 5,123,843
[45] Date of Patent: Jun. 23, 1992

[54] MAGNET ELEMENT FOR A DENTAL PROSTHESIS

[75] Inventors: Joseph M. Van der Zel, Zwaag; Daniel Hamerling, Hoorn, both of Netherlands

[73] Assignee: Elephant Edelmetaal B.V., Hoorn, Netherlands

[21] Appl. No.: 493,874

[22] Filed: Mar. 15, 1990

[30] Foreign Application Priority Data

Mar. 15, 1989 [NL] Netherlands ............... 8900622

[51] Int. Cl.⁵ .................................. A61C 13/235
[52] U.S. Cl. .................................................. 433/189
[58] Field of Search ........................................ 433/189

[56] References Cited
U.S. PATENT DOCUMENTS 4,530,663 7/1985 Portnoy ........................ 433/189
4,857,873 8/1989 Gillings ......................... 433/189

FOREIGN PATENT DOCUMENTS 3140464 4/1983 Fed. Rep. of Germany ...... 433/189

*Primary Examiner*—Gene Mancene
*Assistant Examiner*—Adriene B. Lepiane
*Attorney, Agent, or Firm*—Stevens, Davis, Miller & Mosher

[57] ABSTRACT

A magnet element for a dental prosthesis having a contact surface; a permanent magnet having a first magnet end directed to the contact surface and a second magnet end opposite the first magnet end; and a magnet housing comprising a magnetizable first housing section and a non-magnetizable second housing section. The magnet is only in contact with the first housing section along the second magnet end.

10 Claims, 3 Drawing Sheets

FIG. I

MAGNET ELEMENT FOR A DENTAL PROSTHESIS

This invention relates to a magnet element for a dental prosthesis, comprising:

a contact surface;

a permanent magnet having a first magnet end directed to said contact surface and a second magnet end opposite said first magnet end; and a magnet housing comprising a magnetizable first housing section serving to conduct magnetic field lines from the second magnet end to said contact surface, and a non-magnetizable second housing section serving to allow the passage of magnetic field lines from said second magnet end to said contact surface.

Such a magnet element is described in U.S. Pat. No. 4,530,663, and is used in dental prostheses to achieve retention of the prosthesis in question relative to an upper or lower jaw. To this effect, the magnet element cooperates via the contact surface with a second magnet or a magnetizable member secured in known manner to the jaw, for example, by means of a member implanted in a jaw bone, or a pin mounted in a root canal. The magnet is secured in the housing by pressing it into a chamber in the bottom of the first housing section, and throughout the second magnet end and throughout a portion of the side thereof contacts the first housing section. The first magnet end is spaced from the edge of the first housing section and from the inner wall of the housing section.

Formerly, a dental prosthesis, which can replace one or more teeth, was secured to the jaw by means of a mechanical clamping fit. At present, magnet retention is used more and more in addition to the mechanical clamping fit, because it has been found that the jaw bone decreases in size in the course of time when natural teeth have been removed, so that, after some time, a dental prosthesis secured to the jaw merely on the basis of a mechanical clamping fit comes loose. This results not only in inconvenience to the user, but also in the occurrence of lateral forces on the implants and/or on the remaining teeth, which lateral forces may be destructive. To minimize these lateral forces, a dental element comprises one or more magnet elements of the above kind, which increases the convenience in use of the dental prosthesis.

It will be clear that it is desirable for a combination of magnet and magnetizable member to be geared to each other in such a manner that as great a magnetic attraction as possible is achieved between them, in which connection the maximum permissible dimensions of the magnet element are limited by the space available in the dental prosthesis, which generally will be several millimeters only. The space available to the magnet element should become available to the magnet as best as possible, while the housing should occupy as little space as possible. A first disadvantage of the known magnet element is that its housing is rather bulky. A related disadvantage is that the length of the path covered by the magnetic flux in the second housing section is relatively long, because the first magnet end is spaced from the edge of the first housing section. In designing a dental prosthesis, non-technical factors play a role, too. Although researchers are generally of the opinion that constant magnetic fields are harmless to human tissue, there are publications which suggest that magnetic fields may have an adverse effect on tissues. The result is that the public is reluctant to use parts causing a magnetic field in the mouth. To avoid this objection, the known magnet element is of the closed-field type, which means that the magnetic field generated is at least substantially completely enclosed within the magnet element, so that there is virtually no magnetic field in the mouth cavity and the surrounding tissue. When the dental prosthesis is in the correct position in the mouth, the contact surface of the magnet element bears on the magnetizable member secured to the jaw, thereby to bring about an effective transfer of the magnetic flux from the magnetic element to the magnetizable member. The magnetic field lines extend from the first magnet end through the first housing section, via the contact face between the first housing section and the magnetizable member to the magnetizable member, through the magnetizable member, via the contact face between the second housing section and the magnetizable member to the second housing section, and via the second housing section back to the magnet.

It is known that the magnetic attraction between two magnets in an open-field configuration is greatly dependent on the distance between the two magnets: see, for example, the publication by Tsutsui at al in J Dent Res, 58 (6), June 1979, p. 1601, FIG. 4. In the ideal case, this distance will be zero, but, for example, owing to dimensional tolerances or as a result of resorption of the jaw bone, the accuracy of the fit may decrease, resulting in a marked reduction of the retention forces. It has been found that the degree of distance sensitivity is much greater in a closed-field configuration than in an open-field configuration. Thus it has been found to be a disadvantage of the closed-field configuration of the known magnet element that the magnetic attraction achieved by the known magnet element is greatly dependent on the distance between the contact surface and the magnetizable member than would be the case if an open-field configuration had been used. Another disadvantage of the known magnet element is that the magnetizable first housing section is made of stainless steel, which causes serious corrosion problems in the mouth. A further disadvantage of the known magnet element is that it has a cylindrical shape, which causes an elevation in the dental prosthesis on the side of the tongue which is experienced as irritant, and on the outside of the dental prosthesis has an adverse effect in the placement of artificial teeth.

SUMMARY OF THE INVENTION

It is an object of the present invention to provide a device of the above kind which does not have the disadvantages outlined above. To this effect, a magnet element of the above kind is characterized according to the invention that the magnet is only in contact with the first housing section along the second magnet end. It is thus ensured that the transfer of magnetic flux from the second magnet end to the first housing section takes place through the second magnet end.

Preferably, the magnet has a smaller transverse size at the second magnet end than at the first magnet end, for example, because at least near the second magnet end the magnet has a conical configuration, when it is an advantage when the first housing section has a conical configuration near the second magnet end. It is thus ensured that the transfer of magnetic flux from the second magnet end to the first housing section is effected through the central part of the second magnet end, while also a shorter path is offered for the path to be covered by the magnetic flux through the first housing section.

To ensure that there is a gap of uniform dimensions between the magnet and the first housing section, a positioning means of a non-magnetizable material may be provided between the side wall of the magnet and the first housing section.

Preferably, the first magnet end is at a level with the edge of the first housing section, so that the path covered by the magnet flux in the first housing section may be as short as possible.

In a further preferred embodiment of the present invention, the magnet element is provided in the vicinity of the second magnet end with a third housing section which at least partially encloses the first housing section. The first housing section is thus screened from buccal fluids, while the third housing section may be made of a material that is easier to process than the magnet. The third housing section may for example be provided with at least one sloping surface extending in a first direction to prevent inconvenient elevations of the magnet element in the dental prosthesis, while the third housing section may be provided with retention means, for example, jutting portions, in a direction perpendicular to the first direction, to provide extra retention of the magnet element in the dental prosthesis.

In order that the magnet element may be held together and sealed in a simple manner, the third housing section may be provided with an attachment portion, with the second housing section being in engagement with said attachment portion. The magnet element according to the invention does not have the disadvantages of the known magnet element. Specifically, the magnet element according to this invention combines an advantage of the closed-field configuration, namely, the fact that there is no external magnetic field, with an advantage of an open-field configuration, namely, a more favourable distance-sensitivity of the magnetic attraction.

BRIEF DESCRIPTION OF THE DRAWINGS

The invention will be illustrated in more detail hereinafter by a description of a preferred embodiment of the magnet element according to the invention, by way of example, with reference to the accompanying drawings. In said drawings.

DESCRIPTION OF THE PREFERRED EMBODIMENTS

Figure 1:
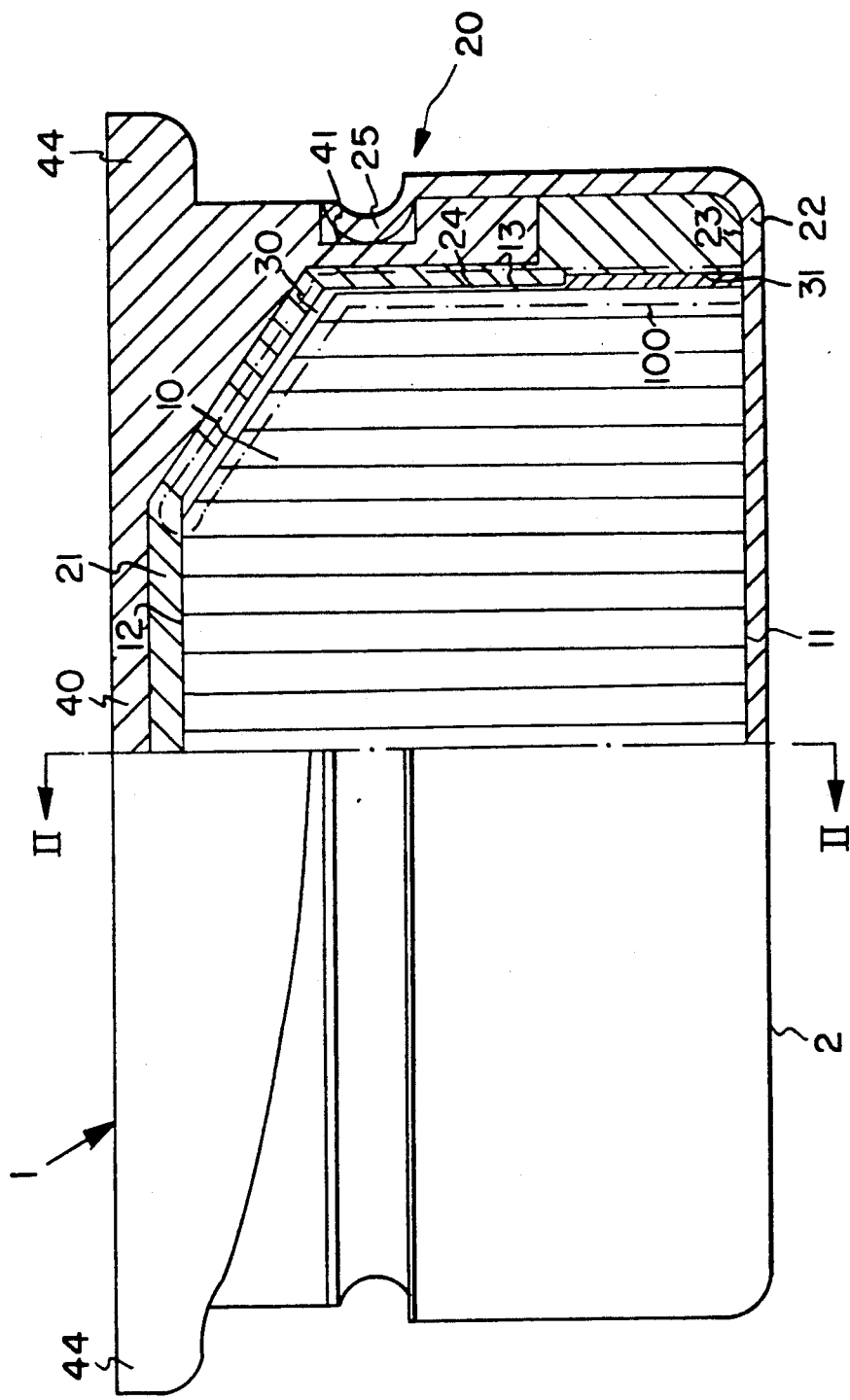
FIG. 1 shows a part-sectional side-elevational view of a preferred embodiment of the magnet element according to the present invention.
Figure 2:
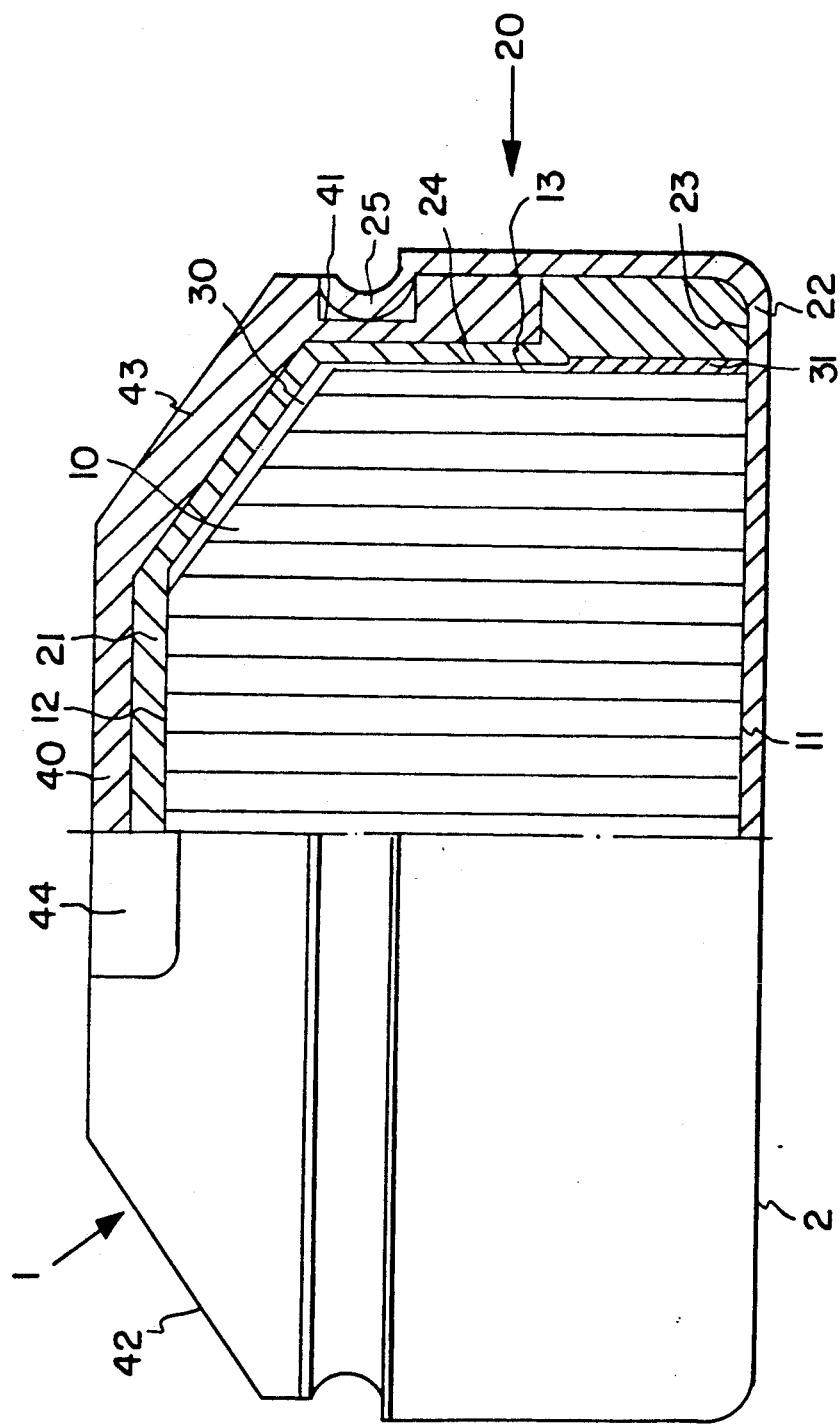
FIG. 2 shows a part-sectional side-elevational view, taken on the line II—II of FIG. 1.

In FIGS. 1 and 2 a magnet element according to the present invention is generally designated by reference numeral 1. The magnet element 1 has a contact surface 2 to make contact with a magnetizable member (not shown) secured to a jaw. Magnet element 1 comprises a permanent magnet 10 with a first magnet end 11 directed to the contact surface 2, and a second magnet end 12 located opposite the first magnet end. Magnet 10 is housed in a magnet housing 20 which comprises a magnetizable first housing section 21 and a non-magnetizable second housing section 22. Magnet 10, first housing section 21, and second housing section 22 are rotationally symmetrical. The first housing section 21 encloses magnet 10 along the second magnet end 12 and the side wall 13, and the first housing section 21 only touches magnet 10 along the second magnet end 12, and in which edge 23 of the first housing section 21 is at a level with the first magnet end 11. Thus there is a gap 30 between the side wall 13 of magnet 10 and the inner wall 24 of the first housing section 21. Disposed within gap 30, in the vicinity of the first magnet end 11, is a positioning means 31 of a non-magnetizable material, for example an aluminium ring, serving to centre the magnet 10 within the first housing section 21, and thus to ensure the existence of a uniform gap.

At least at the second magnet end 12, magnet 10 has a conical form, so that the second magnet end 12 is of smaller diameter than the first magnet end 11. One advantage of this is that the transfer of the magnetic flux from the second magnet end 12 to the first housing section 21 is concentrated in the centre of the second magnet end 12, which has been found to be favourable for a correct flux distribution in the first housing section 21. On the other hand this offers the possibility of giving magnet element 1 a favourable external shape, as will be clarified hereinafter.

The first housing section 21, which is made for example of a known per se cobalt-nickle-iron alloy, suitable for conducting magnetic flux, conducts the magnetic flux from the second magnet end 12 to the contact surface 2. FIG. 1 shows the course of a magnetic field line 100, assuming that the magnet 10 has a magnetic south pole at the first magnet end 11 and a magnetic north pole at the second magnet end 12. The magnetic field line 100 goes in magnet 10 from the south pole to the north pole, leaves the magnet 10 at the central part of the second magnet end 12 for the first housing section 21, and through the first housing section 21, through the second housing section 22, to the contact surface 2. When contact surface 2 of magnet element 10 is in the vicinity of the magnetizable member not shown, the magnetic field line 100 is closed in this magnetizable member to return through the second housing section 22 to the first magnet end 11. As the first housing section 21 is a good magnetic flux conductor, there is no magnetic field outside the first housing section 21 on the side of the second magnet end 12.

Magnet element 1 is further provided with a third housing section 40 which partly encloses the first housing section 21. The third housing section 40 is provided with an attachment slot 41. The second housing section 22 has in cross-section the shape of a capital U, the edge 25 of which is pressed in attachment slot 41, so that the magnet element 1 is held together. The second housing section 22 and the third housing section 40 are made of a corrosion-resistant, non-magnetizable material, such as titanium, palladium or a palladium-copper alloy, so that the first housing section 21 is fully surrounded by corrosion-resistant material, and no corrosion problems will occur at magnet element 1 according to this invention.

As the second housing section 22 according to the invention may be very thin, for example, 0.075 mm, the overall height of the magnet element 1 according to the invention may be small, namely, just a little larger than the height of magnet 10, while the minimum distance of magnet 10 from the magnetizable member not shown has been reduced to the above thickness of the second housing section 22. As a consequence, in order to provide a magnetic attraction which is comparable to the magnetic attraction of the known magnet element, the height of magnet 10 can be reduced relative to the known magnet, so that a further reduction of the overall height of magnet element 1 is provided.

Figure 3:
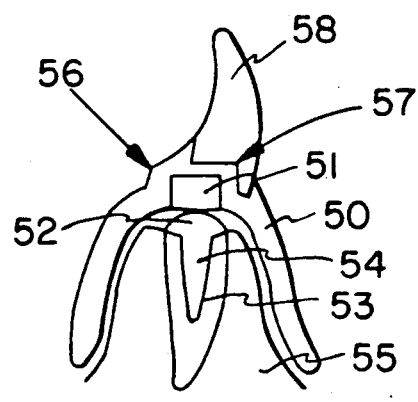
FIG. 3 shows a schematic cross-sectional view through a known magnet element, mounted in a dental prosthesis.
Figure 4:
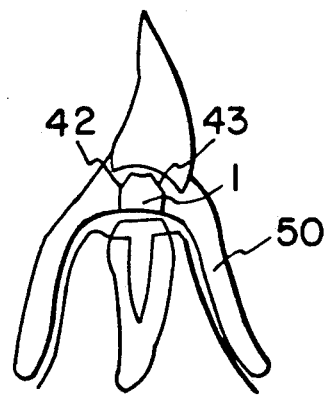
FIG. 4 shows a schematic cross-sectional view through a magnet element according to the present invention, mounted in a dental prosthesis.

The third housing section 40 is not rotationally symmetrical, but is provided with two opposite sloping faces 42, 43, the slope of which, in this example, is the same as the slope of the conical end of magnet 10. Furthermore, the third housing section 40 is provided with jutting retention means 44. The advantage of this will be explained with reference to FIGS. 3 and 4. FIG. 3 shows a known magnet element 51 with a cylindrical shape, mounted in a dental prosthesis 50. Magnet element 51 cooperates with a magnetizable member 52, which through a pin 54 mounted in a root canal 53, is secured to a jaw 55. In the mouth, the cylindrical shape of the known magnet element 51 causes an elevation 56 in dental prosthesis 50 on the side of the tongue, while magnet element 51 on the outside 57 of prosthesis 50 has an adverse effect in the placement of artificial teeth 58. In FIG. 4, the dental prosthesis 50 is again shown, but the known magnet element 51 has been replaced by magnet element 1 according to this invention. Magnet element 1 is firmly secured to prosthesis 50 through the jutting retention means 44. As the magnet element 1 is provided with sloping surfaces 42, 43 positioned parallel to the jaw bone, the problems described above are prevented.

We claim:

1. A magnet element for a dental prosthesis comprising
    a contact surface;
    a permanent magnet having a first magnet end directed to said contact surface, a second magnet end opposite said first magnet end and a side interconnecting said first magnet end with said second magnet end; and
    a magnet housing comprising a magnetizable first housing section enclosing the second magnetic end and side and serving to conduct magnetic field lines from the second magnet end to said contact surface, and a non-magnetizable second housing section serving to allow the passage of magnetic field lines from said second magnet end to said contact surface and a third housing section provided in the vicinity of the second magnet end and at least partially enclosing said first housing section, said magnet being in contact with the first housing section only along the second magnet end.

2. The magnet element as claimed in claim 1, wherein said magnet has a smaller transverse size at the second magnet end than at the first magnet end.

3. The magnet element as claimed in claim 1, wherein near the second magnet end the magnet has a conical configuration.

4. The magnet element as claimed in claim 3, wherein said first housing section has a conical configuration near the second magnet end.

5. The magnet element as claimed in claim 1, wherein an annular positioning means of a non-magnetizable material is provided between the side wall of the magnet and the first housing section.

6. The magnet element as claimed in claim 1, wherein said first magnet end is at a level with the edge of the first housing section.

7. The magnet element as claimed in claim 1, characterized in that the third housing section is provided with at least one sloping surface extending in a first direction.

8. The magnet element as claimed in claim 7, wherein said third housing section is provided with retention means in a direction perpendicular to said first direction.

9. The magnet element as claimed in claim 8, characterized in that said retention means includes jutting portions.

10. The magnet element as claimed in claim 1, wherein said the third housing section includes an attachment portion and that the second housing section is in engagement with said attachment portion.

* * * * *